United States Patent
Bellis et al.

(10) Patent No.: US 8,220,308 B2
(45) Date of Patent: Jul. 17, 2012

(54) SYSTEMS AND METHODS FOR REMOTELY CALIBRATING A GAS SENSOR

(75) Inventors: Peter Damion Bellis, Carson City, NV (US); Ingrid M. Gilstrap, Gardnerville, NV (US); Kristoffer Wayne Wickstead, Carson City, NV (US); Kyle Allan Farwell, Gardnerville, NV (US)

(73) Assignee: General Electric Company, Schenectady, NY (US)

( * ) Notice: Subject to any disclaimer, the term of this patent is extended or adjusted under 35 U.S.C. 154(b) by 355 days.

(21) Appl. No.: 12/567,178

(22) Filed: Sep. 25, 2009

(65) Prior Publication Data

US 2011/0072879 A1 Mar. 31, 2011

(51) Int. Cl.
*G01N 21/00* (2006.01)
(52) U.S. Cl. ........................................................ 73/1.06
(58) Field of Classification Search ................ None
See application file for complete search history.

(56) References Cited

U.S. PATENT DOCUMENTS

| | | | |
|---|---|---|---|
| 4,116,612 A | 9/1978 | Melgaard | |
| 4,151,738 A | 5/1979 | Hyer et al. | |
| 4,384,925 A | 5/1983 | Stetter et al. | |
| 4,462,244 A * | 7/1984 | Lee | 73/1.05 |
| 4,489,590 A | 12/1984 | Hadden | |
| 4,590,789 A | 5/1986 | Kunze | |
| 5,239,492 A | 8/1993 | Hartwig et al. | |
| 6,055,840 A | 5/2000 | Warburton | |
| 6,769,285 B2 * | 8/2004 | Schneider et al. | 73/1.06 |
| 7,437,905 B1 * | 10/2008 | Mueller | 73/1.06 |
| 2007/0186618 A1 * | 8/2007 | Ackerman | 73/1.06 |

FOREIGN PATENT DOCUMENTS

EP 0663594 A1 7/1995

OTHER PUBLICATIONS

General Monitors, "Automatic Remote Gas Calibrator," available at http://www.generalmonitors.com/downloads/literature/combustible/ARGC_DATA.PDF (last visited Sep. 22, 2009).
General Monitors, "High Temperature Remote Gas Calibrator," available at http://www.generalmonitors.com/downloads/literature/combustible/HTRGC_DATA.PDF (last visited Sep. 22, 2009).

* cited by examiner

*Primary Examiner* — Robert R Raevis
(74) *Attorney, Agent, or Firm* — Armstrong Teasdale LLP

(57) ABSTRACT

A method of calibrating a sensor that includes determining a baseline condition of a sensor by channeling a fluid to a remote calibrator assembly coupled to the gas sensor, wherein the remote calibrator assembly includes a calibrator slide. The calibration of the sensor is determined by channeling a calibration fluid to the remote calibrator assembly, wherein during the calibration process, the calibrator slide moves to a calibration position. The calibrator slide moving to an operational position is verified, which is indicative of the sensor being in normal operating condition.

19 Claims, 7 Drawing Sheets

SYSTEMS AND METHODS FOR REMOTELY CALIBRATING A GAS SENSOR

BACKGROUND OF THE INVENTION

This invention relates generally to gas sensor calibrators, and more specifically to systems and methods for remotely calibrating a gas sensor.

Gas turbine engines are used as a power source within a variety of applications. To protect the engine from the environment, and to shield a surrounding environment from the gas turbine engine, at least some known gas turbine engines are contained within an engine assembly compartment that includes an inlet area, an exhaust area, and an engine area that extends between the inlet and exhaust areas.

Within at least some known engine compartments, during operation of the gas turbine engine, a cavity defined within such compartments may include significantly elevated temperatures that are not suitable to enable operators to perform maintenance activities in such compartments. In addition, such compartments often include a hazardous gas detector located in the extraction duct air stream to detect the presence of a fuel leak. At least some known hazardous gas sensors require periodic calibration that is performed in physical contact with the sensor. During calibration, the gas turbine engine is required to be shut down in order to reduce the temperature within the compartment to a temperature suitable to enable an operator to enter the compartment. This known method of calibrating hazardous gas sensors often requires significant periods of time in which the gas turbine engine is not operating. In at least some known gas turbine engines, a shutdown of the gas turbine engine is required every 90 days to facilitate calibrating the hazardous gas sensors. In addition, at least some known sensor calibrators require electronics to facilitate determining a position of the sensor calibrator. Over time, the electronics in at least some known engine compartments may become damaged and result in a reduced operating life of the sensor calibrator due to environmental conditions. In addition, it is not desirable to position additional sources of electrical power within the engine compartment.

Accordingly, it is desirable to provide a method and/or system of calibrating a hazardous gas sensor remotely from outside of the gas engine assembly compartment to facilitate reducing the number of periods and the duration of time during which a gas turbine engine is not operating. Moreover, it is desirable to provide a system that does not require a human operator to enter into the gas engine assembly compartment and that enables the position of the sensor calibrator to be determined without requiring electrical components.

BRIEF DESCRIPTION OF THE INVENTION

In one embodiment, a method of calibrating a gas sensor is presented. The method includes determining a baseline condition of a sensor by channeling a fluid to a remote calibrator assembly coupled to the gas sensor, wherein the remote calibrator assembly includes a calibrator slide. The calibration of the sensor is determined by channeling a calibration fluid to the remote calibrator assembly, wherein during the calibration process, the calibrator slide moves to a calibration position. The calibrator slide moving to an operational position is verified, which is indicative of the sensor being in normal operating condition.

In another embodiment, a sensor calibrator for use in a gas turbine engine is provided. The sensor calibrator includes a calibrator housing and a calibrator slide. The calibrator housing includes an outer surface and an opening defined therein. The calibrator housing is removably coupled to a gas sensor, such that the opening provides flow communication between the gas sensor and ambient air. The calibrator slide includes a cavity defined therein. The calibrator slide is positioned within the calibrator housing. The calibrator slide is slideably coupled to the calibrator housing and is movable between a first position and a second position.

In yet another embodiment, a calibrator assembly is provided. The calibrator assembly includes a sensor coupled to an inner surface of an enclosure. A sensor calibrator is coupled to the sensor. A calibrator canister is coupled to an outer surface of the enclosure, wherein the sensor calibrator is coupled in flow communication with the calibrator canister.

DETAILED DESCRIPTION OF THE INVENTION

The exemplary methods and systems described herein overcome the disadvantages of known sensor calibration methods by providing a remote calibration assembly that enables calibration of a gas sensor without requiring a shutdown of the gas turbine engine. More specifically, the embodiments described herein facilitate calibrating a gas sensor during continuous operation of the gas turbine engine by enabling a user positioned outside of a hazardous or potentially hazardous area to calibrate the sensor. In addition, the embodiments described herein facilitate calibrating a gas sensor without additional electrical equipment required at the sensor.

Figure 1:
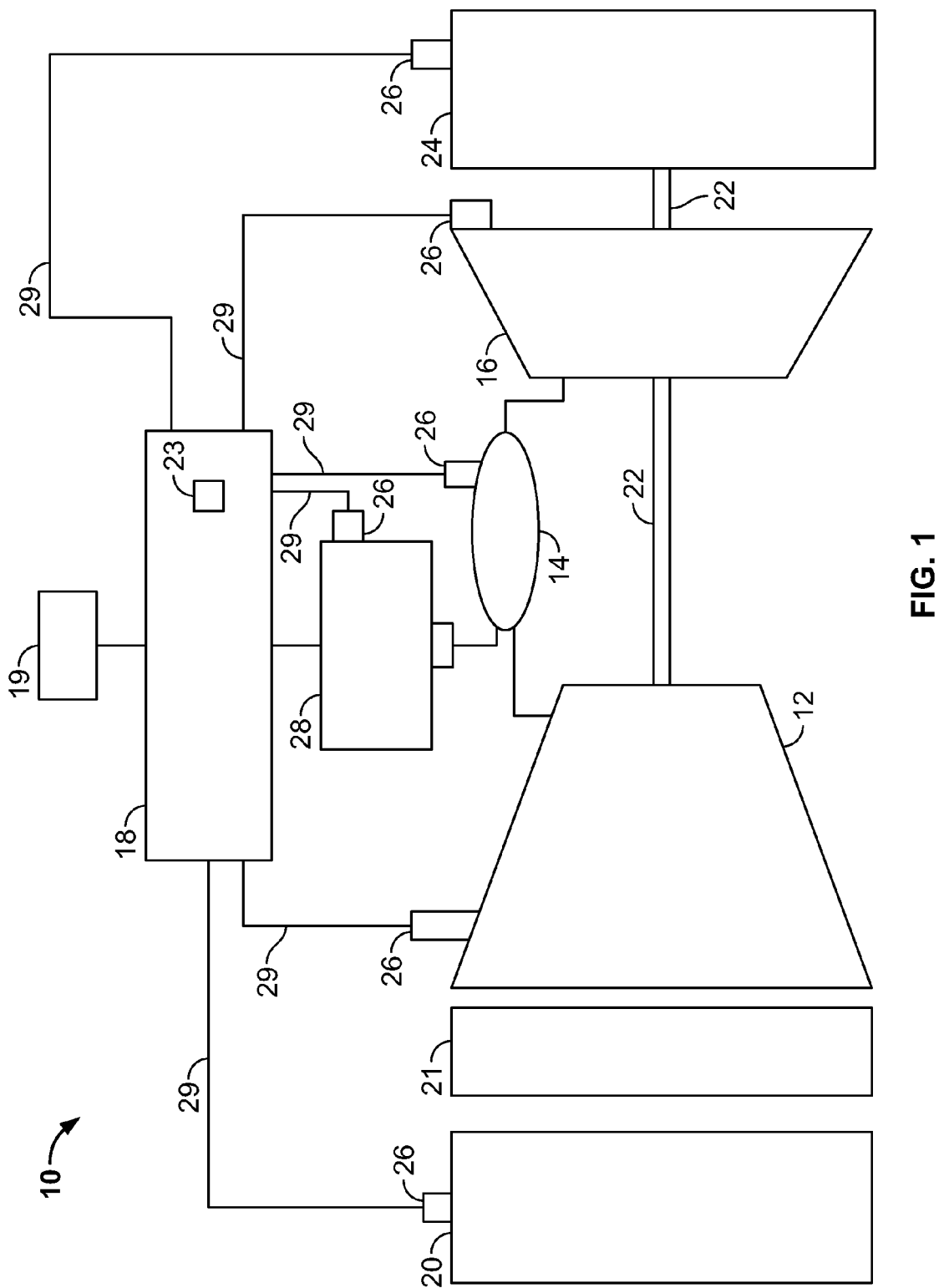
FIG. 1 is a schematic illustration of an exemplary gas turbine engine.

FIG. 1 is a schematic diagram of a gas turbine engine system 10. In the exemplary embodiment, gas turbine engine system 10 includes a compressor 12, a combustor 14, a turbine 16 drivingly coupled to compressor 12 via a rotor shaft 22, a control system or controller 18, and a fuel control assembly 28. Combustor 14 is coupled to compressor 12 such that combustor 14 is in flow communication with compressor 12. Fuel control assembly 28 is coupled to combustor 14 and is configured to channel fuel into combustor 14. An inlet duct 20 channels ambient air to compressor 12. In one embodiment, injected water and/or other humidifying agents are also channeled to compressor 12 through inlet duct 20. Inlet duct 20 may include multiple ducts, filters, screens and/or sound-absorbing devices that contribute to pressure losses of ambient air flowing through inlet duct 20 into one or more inlet guide vanes 21 of compressor 12.

During operation, inlet duct 20 channels air towards compressor 12 that compresses the inlet air to higher pressures and temperatures. Compressor 12 discharges compressed air towards combustor 14 wherein it is mixed with fuel and ignited to generate combustion gases that flow to turbine 16, which drives compressor 12. Combustor 14 channels combustion gases to turbine 16 wherein gas stream thermal energy is converted to mechanical rotational energy.

In the exemplary embodiment, gas turbine engine system 10 may be used to drive a load 24, such as a generator coupled to rotor shaft 22. In an alternative embodiment, generator 24 may be coupled to a forward extension (not shown) of rotor shaft 22.

The operation of gas turbine engine system 10 may be monitored by several sensors 26 that detect various conditions of turbine 16, generator 24, and/or ambient environment. For example, hazardous gas sensors 26 may monitor ambient air surrounding gas turbine engine system 10 for determining the presence of combustible gases, and/or toxic gases. Pressure sensors 26 may monitor ambient pressure and static and dynamic pressure levels at inlet duct 20 to compressor 12 and/or at other locations in the gas stream defined within gas turbine engine system 10. Humidity sensors 26, such as wet and dry bulb thermometers, measure ambient humidity at the inlet duct 20. Sensors 26 may also include flow sensors, speed sensors, flame detector sensors, valve position sensors, guide vane angle sensors, and/or other sensors that sense various parameters relative to the operation of gas turbine engine system 10. As used herein, the term "parameters" refers to physical properties whose values can be used to define the operating conditions of gas turbine engine system 10, such as temperatures, pressures, and gas flows at defined locations.

In the exemplary embodiment, control system 18 communicates with sensors 26 via communication links 29, which may be implemented in hardware and/or software. In one embodiment, communication links 29 remotely communicate data signals to and from control system 18 in accordance with any wired or wireless communication protocol known to one of ordinary skill in the art guided by the teachings herein. Such data signals may include signals indicative of operating conditions of sensors 26 transmitted to the control system 18 and various command signals communicated by control system 18 to sensors 26.

Control system 18 may be a computer system that includes a display 19 and at least one processor 23. Control system 18 executes programs to control the operation of gas turbine engine system 10 using sensor inputs and instructions from human operators. Programs executed by control system 18 may include, for example, calibrating algorithms for calibrating gas sensors 26. User input functionality is provided in display 19, which acts as a user input selection device. In the exemplary embodiment, display 19 is responsive to the user pressing contact on display 19 to selectively perform functionality. Display 19 may also include a keypad which operates in a conventional well known manner. Thus, the user can operate desired functions available with control system 18 by contacting a surface of display 19. Commands generated by control system 18 cause gas sensors 26 to monitor the ambient environment for the presence of combustible zones, toxic zones, and/or oxygen deficient zones, and to activate other control settings on gas turbine engine system 10.

In the embodiments described herein, memory may include, without limitation, a computer-readable medium, such as a random access memory (RAM), and a computer-readable non-volatile medium, such as a flash memory. Alternatively, a floppy disk, a compact disc-read only memory (CD-ROM), a magneto-optical disk (MOD), and/or a digital versatile disc (DVD) may also be used. Also, in the embodiments described herein, input channels include, without limitation, sensors and/or computer peripherals associated with an operator interface. Further, in the exemplary embodiment, output channels may include, without limitation, a control device, an operator interface monitor and/or a display.

Figure 2:
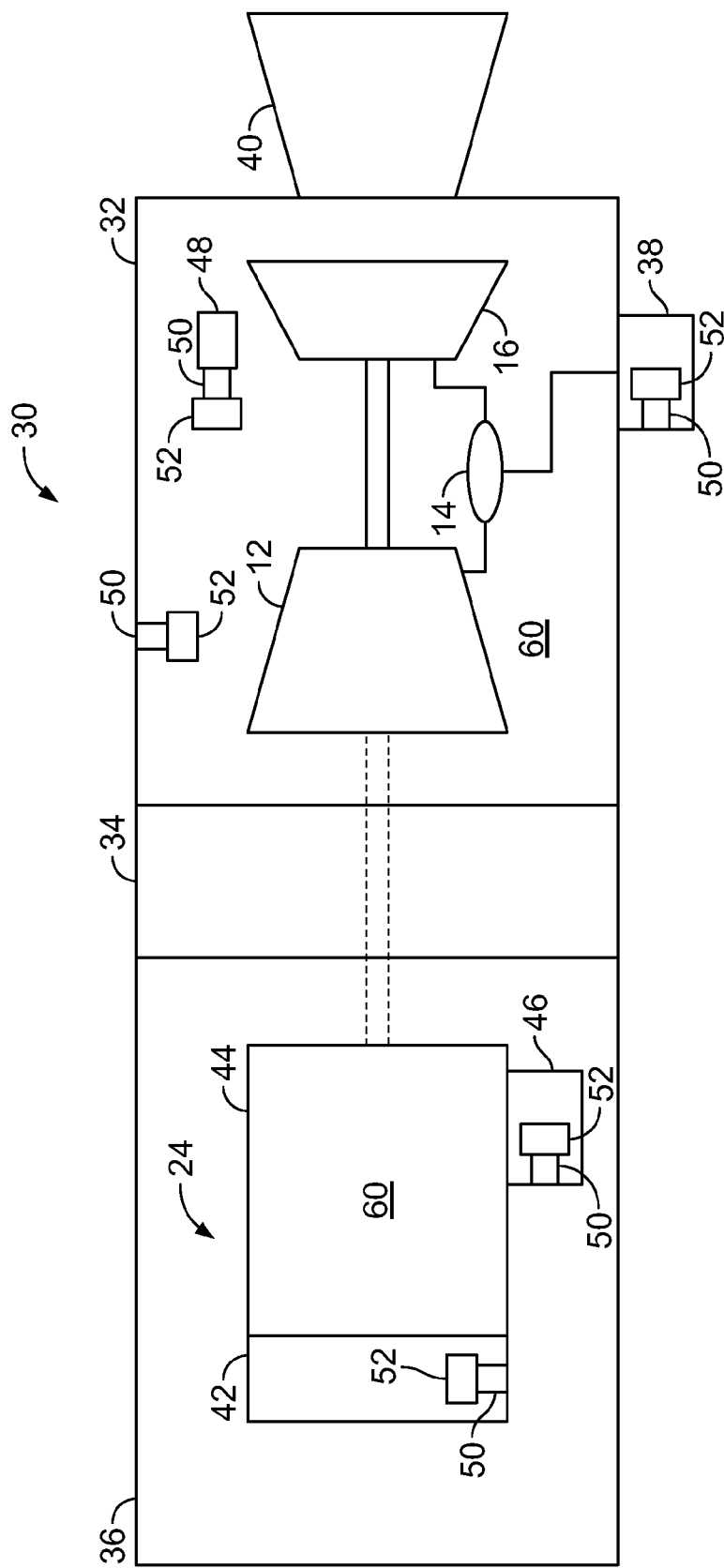
FIG. 2 is a schematic view of an exemplary gas turbine generator compartment that may be used with the turbine engine shown in FIG. 1.

Processors described herein process information transmitted from a plurality of electrical and electronic devices that may include, without limitation, sensors, actuators, compressors, control systems, and/or monitoring devices. Such processors may be physically located in, for example, a control system, a sensor, a monitoring device, a desktop computer, a laptop computer, a programmable logic controller (PLC) cabinet, and/or a distributed control system (DCS) cabinet. RAM and storage devices store and transfer information and instructions to be executed by the processor(s). RAM and storage devices can also be used to store and provide temporary variables, static (i.e., non-changing) information and instructions, or other intermediate information to the processors during execution of instructions by the processor(s). Instructions that are executed may include, without limitation, flow control system control commands. The execution of sequences of instructions is not limited to any specific combination of hardware circuitry and software instructions FIG. 2 is a schematic view of an exemplary compartment 30 that may be used with gas turbine engine system 10. Components shown in FIG. 1 are labeled with similar reference numbers in FIG. 2. In the exemplary embodiment, compartment 30 includes a gas turbine compartment 32, a load shaft compartment 34, a generator compartment 36, a gas fuel module 38, and an exhaust system 40. In the exemplary embodiment, generator 24 is positioned within generator compartment 36. Compressor 12, combustor 14, and turbine 16 are each positioned within gas turbine compartment 32. Generator 24 includes a collector end 42, a generator enclosure 44, and a terminal enclosure 46. Gas turbine compartment 32 includes a ventilation duct 48. A plurality of gas sensors 50 is positioned within compartment 30 and in flow communication with ambient air 60 contain in compartment 30. A plurality of remote calibrator assemblies 52 is each coupled to a corresponding gas sensor 50 for calibrating the gas sensor 50. In the exemplary embodiment, gas sensors 50 are positioned in flow communication with each of ventilation duct 48, gas turbine compartment 32, gas fuel module 38, generator terminal enclosure 46, and collector end 42. In an alternative embodiment, gas sensors 50 are positioned in locations determined by a computational fluid dynamics (CFD) analysis. Gas sensors 50 transmit signals to control system 18 that are indicative of a concentration of gas measured at each respective detector.

Figure 3:
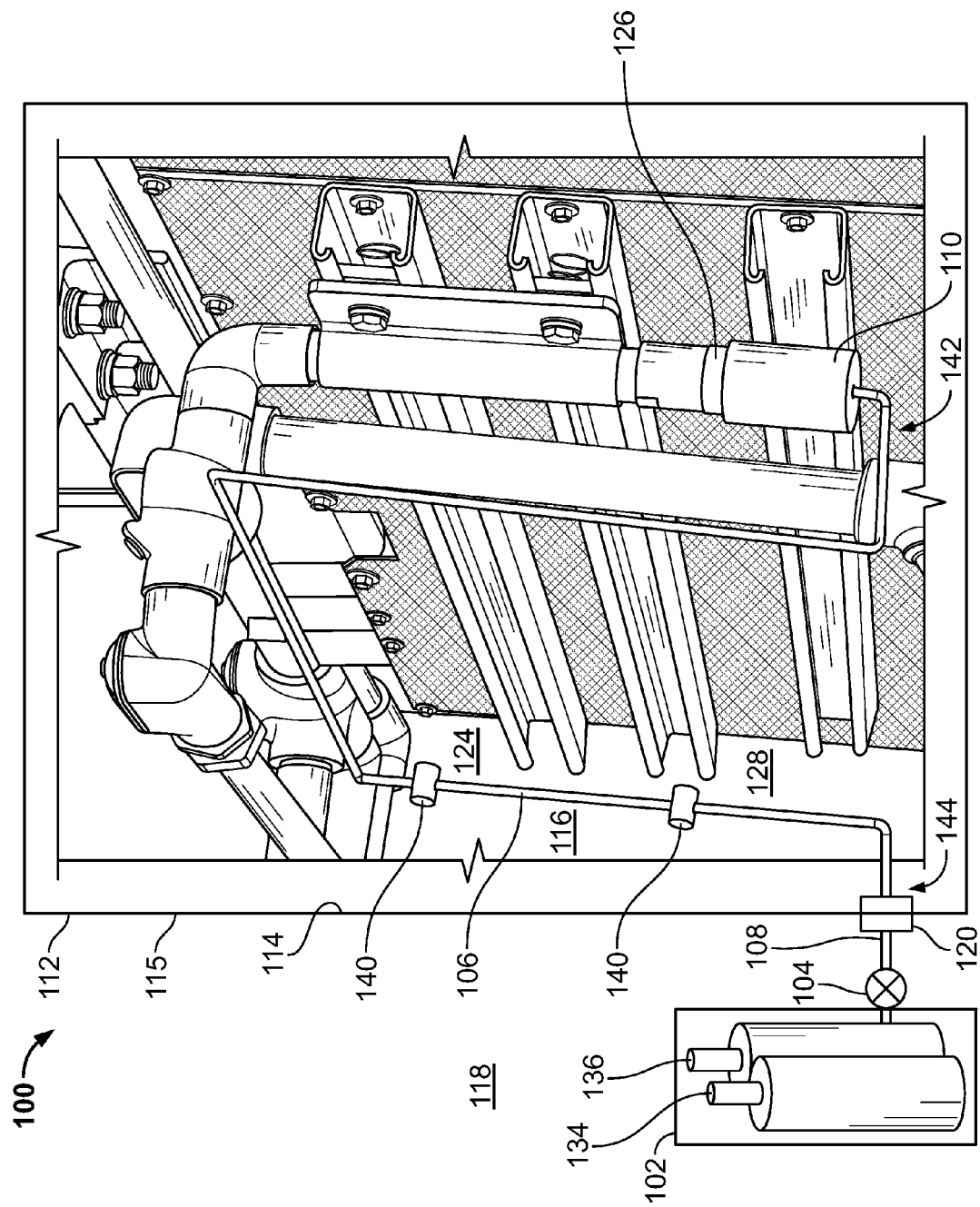
FIG. 3 is a perspective view of an exemplary remote calibrator assembly that may be used with the turbine engine shown in FIG. 1.

FIG. 3 is a schematic view of an exemplary remote calibrator assembly 100 that may be used with gas turbine engine system 10. In the exemplary embodiment, remote calibrator assembly 100 includes a calibration gas canister 102, a gas regulator 104, interior gas line 106, exterior gas line 108, and a sensor calibrator 110. Gas turbine engine system 10 includes an enclosure 112 that surrounds gas turbine engine system 10 and includes an inner surface 114 and an outer surface 115. Inner surface 114 defines an interior area 116. Outer surface 115 defines an exterior area 118. Interior area 116 includes a temperature, $t_1$. In the exemplary embodiment, during operation of gas turbine engine system 10 temperature, $t_1$ is greater than 150° C., which may cause interior area 116 to include a hazardous environment for the operator.

Enclosure 112 includes an outlet port 120 that provides flow communication between interior area 116 and exterior area 118. A gas sensor 126 is positioned within interior area 116 for detecting a hazardous gas 128 that may be present within enclosure 112. In the exemplary embodiment, hazardous gas 128 may be one of methane and/or hydrogen. In an alternative embodiment, hazardous gas 128 may be any substance within interior area 116, such that interior area 116 includes one of a combustible zone, a toxic zone, and/or an oxygen deficient zone.

Sensor calibrator 110 is coupled to gas sensor 126, such that gas sensor 126 is in flow communication with ambient air 124. Interior gas line 106 is coupled to sensor calibrator 110 for channeling a calibration gas 134 and/or a clean gas 136 to sensor calibrator 110. Interior gas line 106 is positioned adjacent to inner surface 114 and is mounted to inner surface 114 using a plurality of fasteners 140. In the exemplary embodiment, interior gas line 106 includes a first end 142 and a second end 144. First end 142 is coupled to sensor calibrator 110 and second end 144 is coupled to outlet port 120, such that sensor calibrator 110 is in flow communication with an exterior area 118. In the exemplary embodiment, calibration gas canister 102 and exterior gas line 108 are positioned in exterior area 118. Exterior gas line 108 is coupled to gas regulator 104 and to outlet port 120, such that calibration gas canister 102 is in flow communication with sensor calibrator 110. Calibration gas canister 102 includes at least one of calibration gas 134 and/or clean gas 136.

During operation of remote calibrator assembly 100, gas regulator 104 is moved between a first, or closed position to a second, or open position to allow a flow of clean gas 136 to be channeled to sensor calibrator 110 through exterior gas line 108 and interior gas line 106. Sensor calibrator 110 channels clean gas 136 to gas sensor 126. Upon contact with clean gas 136, gas sensor 126 sends a signal to control system 18. Control system 18 determines that clean gas has been detected by gas sensor 126 and provides an indication to the user. Gas regulator 104 is then moved to the closed position to prevent a flow of clean gas 136 to gas sensor 126. Gas regulator 104 is then moved to the open position to allow a flow of calibration gas 134 to be channeled to sensor calibrator 110. Upon contact with calibration gas 134, gas sensor 126 sends a signal to control system 18, which then determines that calibration gas 134 has been detected. Control system 18 provides an indication to the user that calibration gas 134 has been detected and gas sensor 126 has been calibrated. Control system 18 instructs the user to remove the flow of calibration gas 134 from gas sensor 126 and monitors a signal from gas sensor 126. Control system 18 verifies gas sensor 126 is in flow communication with ambient air 124 and provides an indication of such to the user. In the exemplary embodiment, control system 18 verifies that gas sensor 126 is in flow communication with ambient air 124 by monitoring a signal from gas sensor 126 for a specified period of time. Control system 18 determines the signal has reached a specified signal strength during the period of time. In an alternative embodiment, control system 18 verifies that gas sensor 126 is in flow communication with ambient air 124 by receiving a signal from gas sensor 126 after a specified period of time and determining the signal represents ambient air 124.

Figure 4:
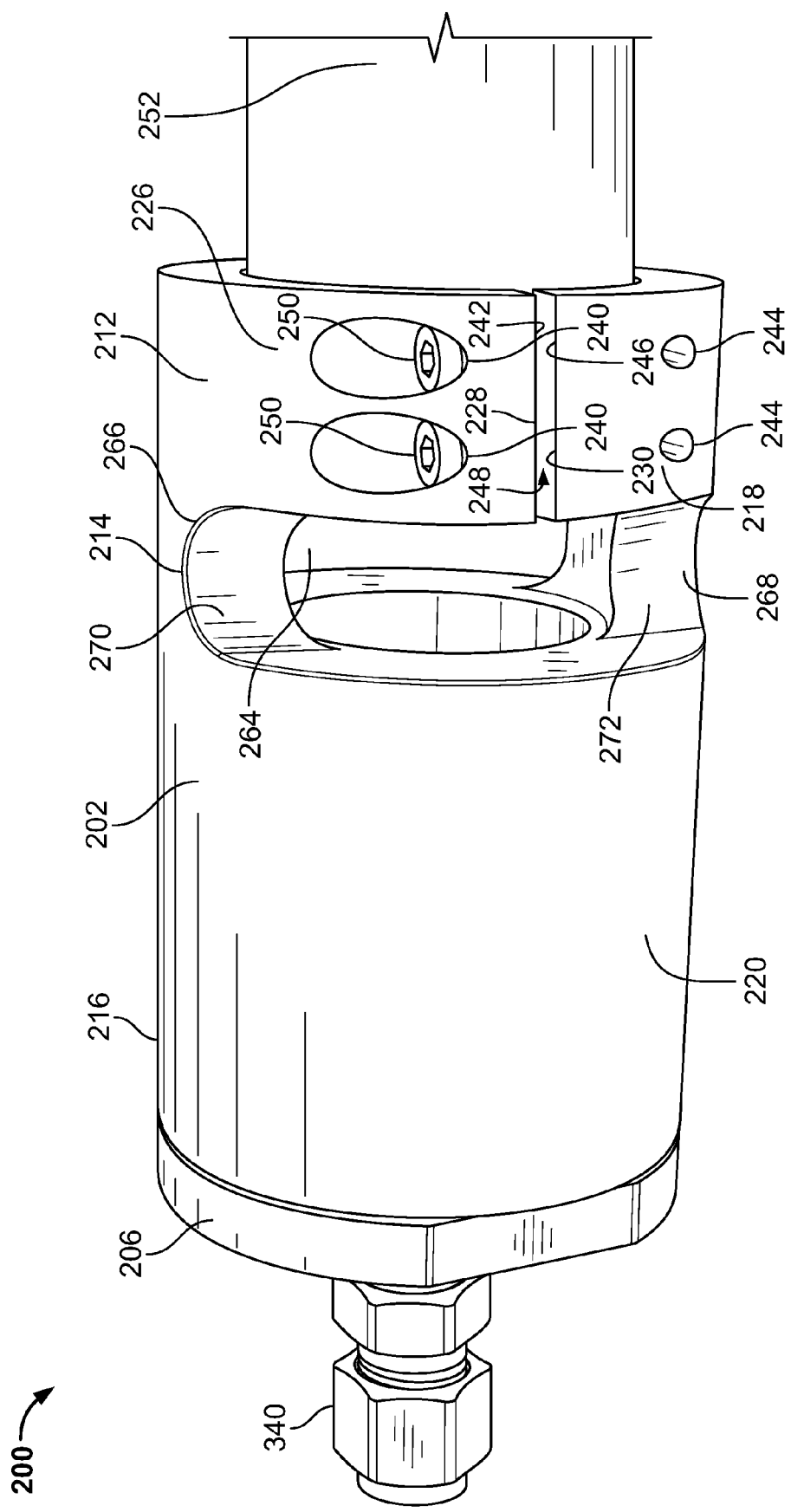
FIG. 4 is a perspective view of an alternative exemplary remote calibrator that may be used with the turbine engine shown in FIG. 1.
Figure 5:
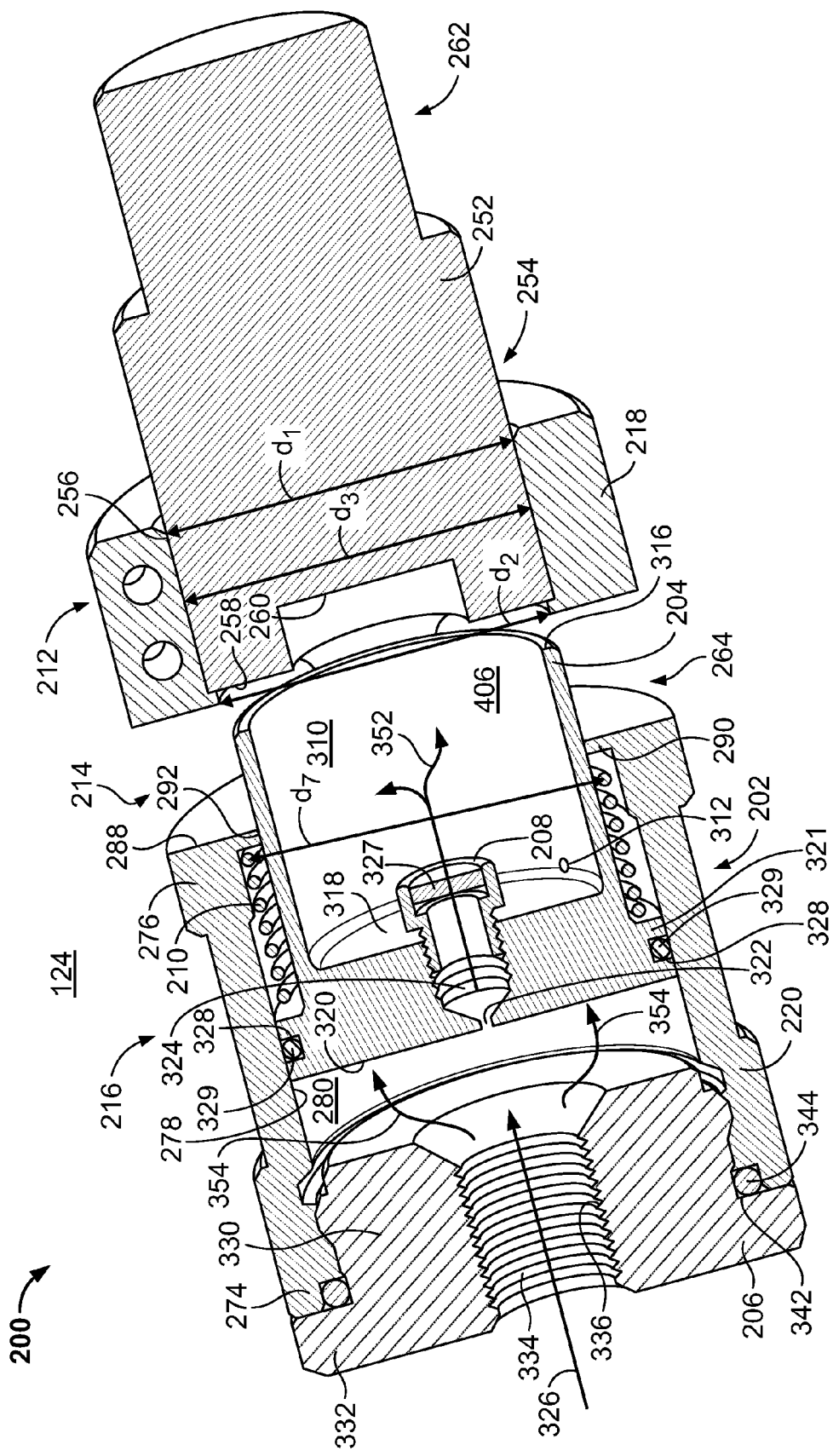
FIG. 5 is an cross-sectional view of the remote calibrator shown in FIG. 4.
Figure 6:
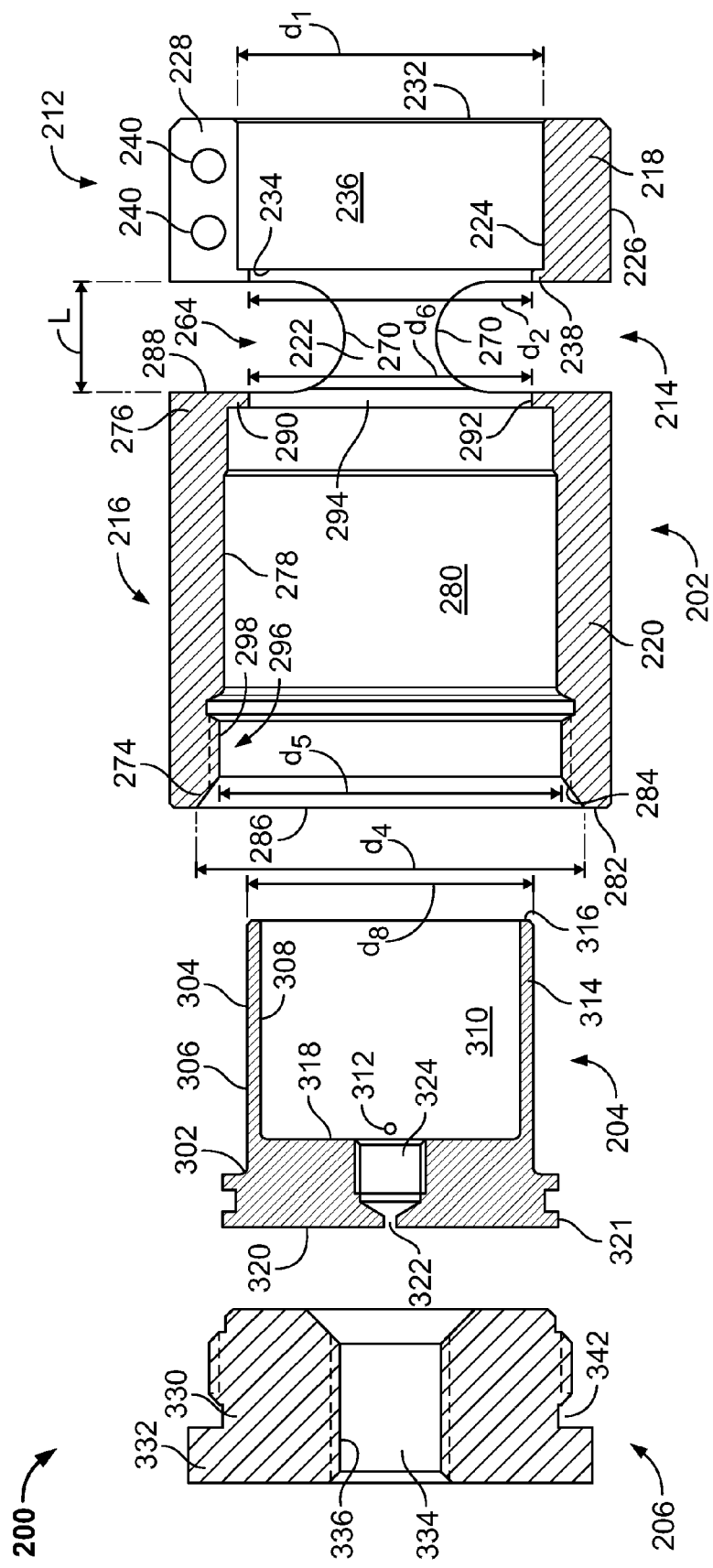
FIG. 6 is an exploded cross-sectional view of the remote calibrator shown in FIG. 4.

FIG. 4 is a perspective view of an exemplary remote calibrator 200 that may be used with gas turbine engine system 10. FIG. 5 is a cross-sectional view of an exemplary sensor calibrator 200 shown in FIG. 4. FIG. 6 is an exploded cross-sectional view of exemplary sensor calibrator 200 shown in FIG. 4. In the exemplary embodiment, sensor calibrator 200 includes a calibrator housing 202, a calibrator slide 204, a cap 206, a diffuser 208, and a spring 210. Calibrator housing 202 includes an upper portion 212, and middle portion 214, and a lower portion 216. Upper portion 212 includes an upper member 218. Lower portion 216 includes a lower member 220 concentrically aligned with upper member 218. Middle portion 214 includes at least one support arm 222 that extends between upper portion 212 and lower portion 216 and is coupled to upper member 218 and lower member 220. In the exemplary embodiment, calibrator housing 202 is formed unitarily. In an alternative embodiment, middle portion 214 is coupled to upper portion 212 and lower portion 216 via at least one of welds and/or fasteners.

Upper member 218 includes an inner surface 224, an outer surface 226, a first end wall 228, and an opposing second end wall 230 Inner surface 224 includes a first open end 232, a second open end 234, and a cavity 236 defined by inner surface 224 that extends between first open end 232 and second open end 234. First open end 232 includes a first diameter, $d_1$. Second open end 234 includes a circumferentially-spaced shoulder 238 that extends radially inward from inner surface 224 and that includes a second diameter, $d_2$, that is smaller than first diameter, $d_1$. First end wall 228 includes a plurality of openings 240 that extend between a first wall surface 242 and outer surface 226. Second end wall 230 includes an opposing plurality of openings 244 that extend between a second wall surface 246 to outer surface 226. First end wall 228 is positioned adjacent to second end wall 230 such that a gap 248 is defined between first wall surface 242 and second wall surface 246. First wall openings 240 are concentrically aligned to second wall openings 244, such that a plurality of fasters 250 are at least partially inserted through first wall openings 240 and second wall openings 244 to facilitate coupling sensor calibrator 200 to a gas sensor 252.

Gas sensor 252 includes a head portion 254 that includes a substantially cylindrically-shaped outer surface 256. Outer surface 256 includes a third diameter, $d_3$, that is smaller than first diameter, $d_1$, and is larger than second diameter, $d_2$. Head portion 254 includes a forward surface 258 that extends perpendicular to outer surface 256. At least one sensor bore 260 extends inward from forward surface 258 towards a rear portion 262 of gas sensor 252. Sensor bore 260 is concentrically aligned to outer surface 256. In the exemplary embodiment, gas sensor 252 is a catalytic bead sensor, however, it should be recognized that gas sensor 252 may be any sensor that requires calibration.

In the exemplary embodiment, gas sensor 252 is removably coupled to sensor calibrator 200, wherein gas sensor 252 is inserted through first open end 232 towards second open end 234. Gas sensor 252 is positioned within cavity 236, such that forward surface 258 is adjacent to shoulder 238, and inner surface 224 is adjacent to outer surface 256. Shoulder 238 is sized and shaped to facilitate preventing gas sensor 252 from moving through second open end 234. Fasteners 250 facilitate urging first end wall 228 towards second end wall 230, wherein gap 248 is facilitated to be reduced, wherein inner surface 224 is in frictional contact with outer surface 256, such that gas sensor 252 is coupled to sensor calibrator 200 via a friction fit.

Middle portion 214 includes at least one support arm 222 that extends between upper portion 212 and lower portion 216, and is coupled to upper member 218 and lower member 220. Support arm 222 includes a length L, such that an opening 264 is defined between upper portion 212 and lower portion 216. In the exemplary embodiment, middle portion 214 includes a first support arm 266 and an opposing second support arm 268. In an alternative embodiment, middle portion 214 includes any number of support arms 222 to enable sensor calibrator 200 to function as described herein. First support arm 266 and second support arm 268 each include length L. First support arm 266 includes arcuate outer surfaces 270 that extend between upper portion 212 and lower portion 216. Second support arm 268 includes arcuate outer surface 272 that extend between upper portion 212 and lower portion 216. In an alternative embodiment, outer surfaces 270 and 272 include any shape that enables sensor calibrator 200 to function as described herein.

Lower portion 216 includes a first end wall 274, an opposing second end wall 276, and lower member 220 that extends between first end wall 274 and second end wall 276. Lower member 220 includes a substantially cylindrical inner surface 278 that defines a cavity 280. First end wall 274 includes a first end wall outer surface 282 and an obliquely angled interior surface 284 that defines a first opening 286 having a frustoconical shape that extends from first end wall outer surface 282 towards second end wall 276. First opening 286 includes an outer diameter, $d_4$, and an inner diameter, $d_5$, which is smaller than $d_4$. First opening 286 is sized and shaped to receive cap 206 therein. Second end wall 276 includes an outer surface 288 and a shoulder 290. Shoulder 290 extends radially inward from second end wall 276 and includes an inner shoulder surface 292 that defines a second opening 294. Second opening 294 extends from second wall outer surface 288 towards first end wall 274 and includes a diameter, $d_6$.

In the exemplary embodiment, calibrator slide 204 is positioned within cavity 280 and is slideably coupled to lower portion 216. More specifically, second opening 294 is sized and shaped to slideably receive calibrator slide 204 therein. Calibrator slide 204 is moveable between a first, or operational position (shown in FIG. 5) and a second, or calibration position (not shown). In the operational position, calibrator slide 204 is positioned within calibrator housing 202, such that opening 264 extends substantially though calibrator housing 202. In the calibration position, calibrator slide 204 extends outward from lower portion 216 towards upper portion 212, such that opening 264 does not extend through calibrator housing 202. In the calibration position, calibrator slide 204 encapsulates gas sensor head portion 254, such that a calibration gas chamber 406 is defined between calibrator slide 204 and gas sensor head portion 254. Spring 210 is positioned within cavity 280 and is positioned between inner surface 278 and calibrator slide 204. Spring 210 is coupled to calibrator slide 204 and lower member 220. More specifically, Spring 210 is coupled to shoulder 290 and is configured to bias calibrator slide 204 towards first end wall 274 and into the first position. Spring 210 includes a diameter, $d_7$, and is sized to receive calibrator slide 204 therein. In the exemplary embodiment, second opening diameter $d_6$ is substantially equal to spring diameter $d_7$, such that second opening 294 is sized to facilitate preventing spring 210 from extending through second opening 294. In the exemplary embodiment, a portion 296 of inner surface 278 includes a threaded surface 298, such that cap 206 is threadably coupled to lower member 220. In an alternative embodiment, cap 206 is coupled to lower member 220 via fasteners, bolts, and/or a weld.

Calibrator slide 204 includes a base member 302 and a substantially cylindrical upper member 304 that extends outward from base member 302. Upper member 304 includes an outer surface 306 and an inner surface 308. Inner surface 308 has a substantially cylindrical shape that defines a cavity 310. Outer surface 306 includes a diameter, $d_8$, that is substantially equal to second opening diameter $d_6$. A vent hole 312 is defined within upper member 304 and extends from inner surface 308 through outer surface 306, such that cavity 310 is in flow communication with cavity 280. Upper member 304 includes a wall 314 that includes an end face 316 that extends between inner surface 308 and outer surface 306. Upper member 304 is coupled to base member 302 such that base member 302 and upper member 304 define cavity 310. Base member 302 includes an inner surface 318, an outer surface 320, and a circumferential outer wall 321. An orifice 322 is defined within base member 302 and extends from outer surface 320 towards inner surface 318. An opening 324 is defined within base member 302 and extends from inner surface 318 towards outer surface 320. Opening 324 is concentrically aligned with orifice 322 and is in flow communication with orifice 322, such that cavity 310 is in flow communication with cavity 280. Orifice 322 is sized and shaped to facilitate restricting a flow of fluid 326 though to cavity 310, such that fluid 326 entering cavity 310 has a specified flowrate and a pressure suitable to enable gas sensor 252 to be calibrated. Opening 324 is sized and shaped to receive diffuser 208 therein. In the exemplary embodiment, diffuser 208 includes a porous membrane 327 that is configured to channel fluid 326 such that fluid 326 has a substantially uniform velocity entering cavity 310 suitable to enable gas sensor 252 to be calibrated. Outer wall 321 includes a circumferential groove 328 defined therein. A seal 329 is positioned within groove 328 such that seal 329 is in sealing contract with calibrator housing inner surface 278.

Cap 206 is removably coupled to calibrator housing 202, such that cap 206 and inner surface 308 define cavity 310. Cap 206 includes a base member 330 coupled to an outer wall 332, and an opening 334 defined within base member 330 and outer wall 332. Base member 330 includes a substantially circular shape and is sized such that cap 206 is inserted into first opening 286 of calibrator housing 202. Base member 330 includes a threaded interior surface 336 that defines opening 334 such that a gas line fitting 340 is threadably coupled to base member 330 through opening 334. Gas line fitting 340 is coupled to interior gas line 106 for providing a flow of calibration gas 134 and/or clean gas 136 to sensor calibrator 200. Opening 334 extends through base member 330 and outer wall 332 to provide flow communication between calibration gas canister 102 and cavity 280. Outer wall 332 includes a grove 342 that is sized to received an o-ring 344 positioned between outer wall 332 and calibrator housing 202 such that cap 206 is in sealing contact with calibrator housing 202.

During operation spring 210 biases calibrator slide 204 to the first position. In first position, end face 316 of calibrator slide 204 is positioned adjacent to shoulder 290 such that opening 264 extends substantially through middle portion 214, wherein sensor bore 260 is in flow communication with ambient air 124. Fluid flow 326 is provided from calibration gas canister 102 and is channeled to sensor calibrator 200 via gas lines 106 and 108. As fluid 326 is channeled through opening 334 to cavity 280, a first fluid portion 352 is channeled through orifice 322 to diffuser 208. Orifice 322 is configured to facilitate increasing a flowrate of first fluid portion 352 suitable to enable calibration of gas sensor 252. Diffuser 208 is configured to facilitate providing a substantially uniform velocity to first fluid portion 352 as first fluid portion 352 enters cavity 310. A second fluid portion 354 impinges on outer surface 320 of base member 302 and urges calibrator slide 204 towards gas sensor 252, such that calibrator slide 204 is moved to second position. In second position, end face 316 is in contact with gas sensor forward surface 258, such that sensor bore 260 is positioned within cavity 310. In second position, first fluid portion 352 is in contact with gas sensor 252. Vent hole 312 channels first fluid portion 352 from cavity 310 into ambient air 124. As fluid flow 326 is removed from sensor calibrator 200, spring 210 biases calibrator slide 204 to the first position and the remaining fluid is channeled to ambient air 124 via opening 264.

Figure 7:
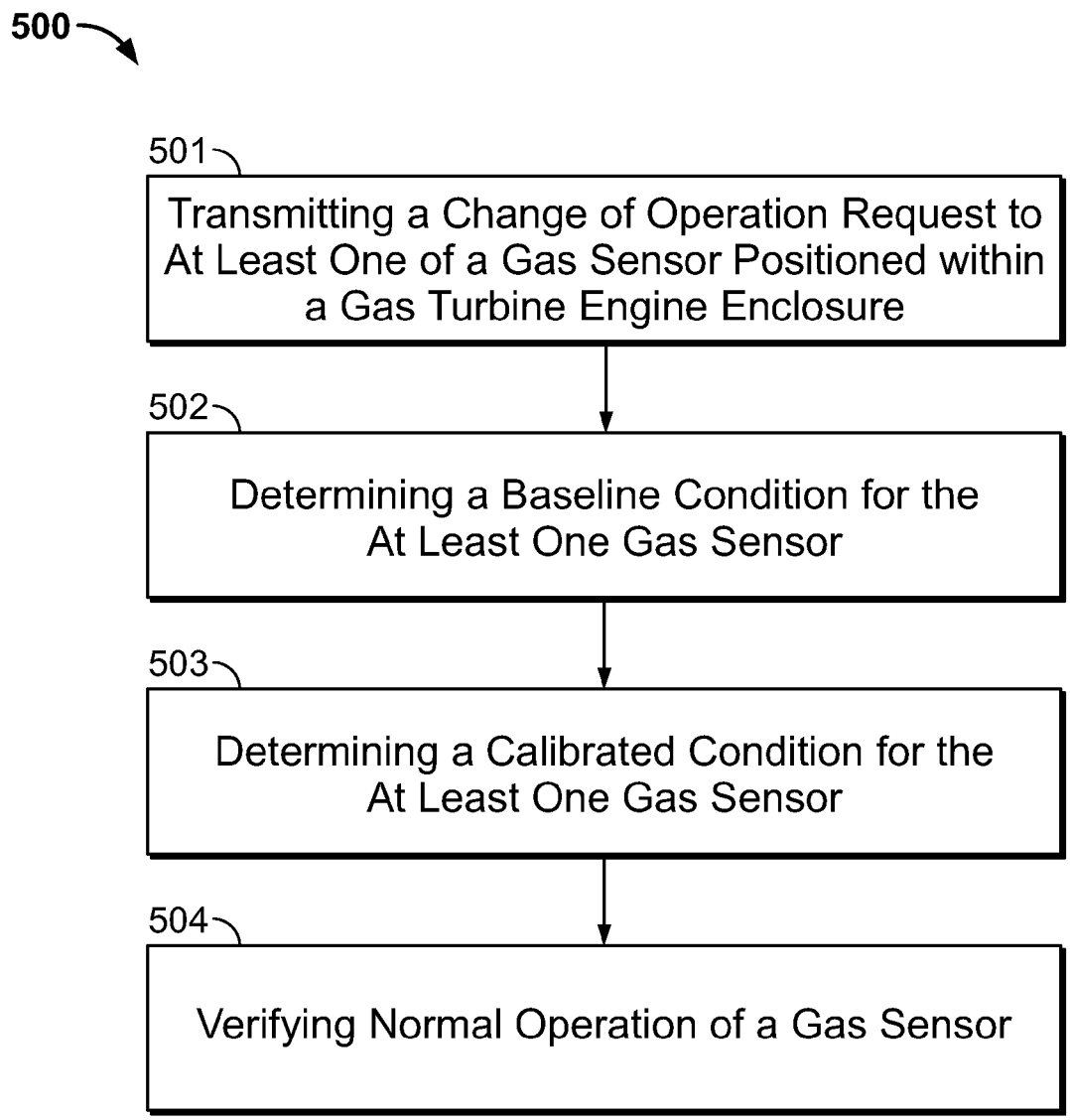
FIG. 7 is a flowchart of an exemplary method of calibrating a gas sensor that may be used with the turbine engine shown in FIG. 1.

FIG. 7 is a flowchart of an exemplary method 500 of calibrating gas sensor 252. Method 500 includes transmitting 501 a change of operation request to gas sensor 126, such that gas sensor 126 is placed in alarm-by-pass mode. In the exemplary embodiment, control system 18 displays a message to the user on display 19 that gas sensor 126 will be moved to a non-alarm state during the calibration. Control system 18 transmits a signal to gas sensor 126 to by-pass operating alarms setpoints, such that gas sensor 126 will not transmit an alarm upon reading a gas having a lower explosive limit (LEL) above operating alarm setpoints. As used herein, the term "lower explosive limit" means a limit at which a fluid may be combustible. The user inputs a calibration non-activity time period, such that control system 18 will return gas sensor 126 to an active alarm state if no user input is received during the specified period of time. Control system 18 requests the user to input a calibration LEL into control system 18. The calibration LEL is the known LEL of calibration gas 134. In the exemplary embodiment, calibration gas 134 includes a LEL of about 50%, however, the user can use a calibration gas having any LEL that enables the calibration process to be performed as described herein.

A baseline condition is determined 502 for gas sensor 126 by channeling a baseline fluid to remote calibrator assembly 100 and to gas sensor 126. In the exemplary embodiment, the baseline fluid is clean gas 136 that is about 0% LEL. Control system 18 instructs the user to channel clean gas 136 to gas sensor 126. The user couples clean gas 136 to remote calibrator assembly 100 through outlet port 120, moves gas regulator 104 to an open position to channel clean gas 136 to sensor calibrator 110, and indicates to control system 18 that clean gas 136 has been channeled to gas sensor 126. Upon contact with clean gas 136, calibrator slide 204 moves to the calibration position such that gas sensor 126 is positioned within chamber 406. Control system 18 instructs gas sensor 126 to obtain an LEL measurement. Gas sensor 126 transmits a signal representative of an environment within chamber 406 to control system 18. Upon receipt of the signal, control system 18 determines whether the signal represents the known clean gas LEL. Upon determining that the signal represents the known clean gas LEL, control system 18 instructs the user to channel calibration gas 134 to remote calibrator assembly 100.

A calibration is then determined 503 for gas sensor 126 by channeling a calibration fluid to gas sensor 126. In the exemplary embodiment, the calibration fluid is calibration gas 134 that is about 50% LEL. The user moves gas regulator 104 to the closed position and uncouples clean gas 136 from remote calibrator assembly 100. The user couples calibration gas 134 to remote calibrator assembly, moves gas regulator 104 to an open position to channel calibration gas 134 to sensor calibrator 110, and indicates to control system 18 that calibration gas 134 has been channeled to gas sensor 126. Upon contact with calibration gas 134, calibrator slide 204 moves to the calibration position such that gas sensor 126 is positioned within chamber 406. Control system 18 instructs gas sensor 126 to obtain an LEL measurement. Gas sensor 126 transmits a signal representative of the environment within chamber 406 to control system 18. Upon receipt of the signal, control system 18 determines whether the signal represents the known calibration gas LEL. Upon determining that the signal represents the known calibration gas LEL, control system 18 instructs to the user to uncouple calibration gas 134 from remote calibrator assembly 100. As calibration gas 134 is uncoupled from remote calibrator assembly 100, spring 210 biases calibrator slide 204 to the operational position, wherein gas sensor 126 is in flow communication with ambient air 124, such that gas sensor 126 is in normal operation.

In the exemplary embodiment, normal operation of gas sensor 126 is verified 504 by control system 18 monitoring a signal transmitted by gas sensor 126 over a specified period of time. As calibration gas 134 is removed from contacting gas sensor 126, calibrator slide 204 moves to the operational position, such that gas sensor 126 is in flow communication with ambient air 124. As gas sensor 126 comes in contact with ambient air 124, the signal transmitted by gas sensor 126 begins to decay. Control system 18 monitors the decay of the signal for a specified period of time and determines whether, after an elapse of the specified time, the signal represents gas sensor 126 normal operating condition. If the signal transmitted by gas sensor 126 decays to a limit that represents normal operation condition within the specified period of time, control system 18 instructs the user that gas sensor 126 is in normal operation. In the exemplary embodiment, control system 18 will monitor the signal transmitted by gas sensor 126 for a period of 40 seconds. In an alternative embodiment, control system 18 receives a signal from gas sensor 126 after an elapse of a specified period of time after calibration gas 134 has been uncoupled, and determines whether the signal represents a normal operating condition of gas sensor 126.

It will be appreciated that a technical effect of the embodiments of the present invention described herein is the reliable calibration of a gas sensor and the determination of the position of a calibrator slide, such that the gas sensor is in flow communication with the monitored environment.

The above-described systems and methods facilitate calibrating a gas sensor positioned within a gas turbine engine enclosure without having a human operator enter a hazardous area. As such, the embodiments described herein facilitate calibrating the gas sensor during operation of the gas turbine engine. Specifically, the remote calibrator assembly facilitates calibrating a gas sensor by applying a calibration gas to the gas sensor from outside the hazardous area and facilitates determining that a calibrator slide has returned to a start position, such that the gas sensor is in flow communication with the ambient air. As such, the cost of maintaining the gas turbine engine assembly is facilitated to be reduced.

Exemplary embodiments of systems and methods for remotely calibrating a gas sensor for use in a gas turbine engine assembly are described above in detail. The systems and methods are not limited to the specific embodiments described herein, but rather, components of systems and/or steps of the method may be utilized independently and separately from other components and/or steps described herein. For example, the systems and method may also be used in combination with other combustion systems and methods, and are not limited to practice with only the gas turbine engine assembly as described herein. Rather, the exemplary embodiment can be implemented and utilized in connection with many other combustion system applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of calibrating a sensor, said method comprising:
   determining a baseline condition of a sensor by channeling a fluid to a remote calibrator assembly coupled to the sensor, wherein the remote calibrator assembly includes a calibrator slide;
   calibrating the sensor by channeling a calibration fluid to the remote calibrator assembly, wherein during the calibration process, the calibrator slide moves to a calibration position; and
   verifying, using a control system, that the calibrator slide has moved to an operational position indicative of the sensor being in normal operating condition.

2. A method in accordance with claim 1 further comprising:
   monitoring a decay of a signal received from the sensor for a specified period of time; and
   determining whether the signal is indicative of a sensor normal operating condition after the specified period of time has elapsed.

3. A method in accordance with claim 1 further comprising:
   receiving a signal from the sensor after a specified period of time; and
   determining whether the signal is indicative of a sensor normal operating condition.

4. A method in accordance with claim 1, wherein verifying the calibrator slide has moved to an operational position further comprises ensuring that the sensor is in flow communication with ambient air.

5. A sensor calibrator for use in an engine system, said sensor calibrator comprising:
   a calibrator housing comprising an outer surface and an opening defined therein, said calibrator housing removably coupled to a sensor, such that said opening provides flow communication between the sensor and ambient air; and
   a calibrator slide comprising a cavity defined therein, said calibrator slide positioned within said calibrator housing, said slide is slideably coupled to said calibrator housing and is movable between a first position and a second position, said slide contacts the sensor in the second position, such that a chamber is defined between said slide and the sensor.

6. A sensor calibrator in accordance with claim 5, wherein said calibration slide is positioned a distance from the sensor in the first position, such that the sensor is in flow communication with ambient air flowing through said calibrator housing opening.

7. A sensor calibrator in accordance with claim 6, wherein said calibrator slide is movable to said second position after said calibrator housing receives a flow of fluid.

8. A sensor calibrator in accordance with claim 5, wherein said calibrator housing further comprises at least one support arm that extends between an upper portion and a lower portion, said opening is defined between said upper portion and said lower portion.

9. A sensor calibrator in accordance with claim 5 further comprising a diffuser coupled to said calibrator slide, said diffuser is positioned within said calibrator slide cavity and is configured to channel a fluid to the sensor at a substantially uniform velocity.

10. A sensor calibrator in accordance with claim 5, wherein said calibrator slide comprises a base member, said base member comprising an orifice defined within said base member, said orifice configured to channel a fluid to the sensor at a predetermined flowrate.

11. A sensor calibrator in accordance with claim 5 further comprising a biasing mechanism positioned between said calibrator housing inner surface and said calibrator slide for biasing said calibrator slide away from the sensor.

12. A sensor calibrator in accordance with claim 5 further comprising a cap coupled to said calibrator housing, said cap comprising an opening defined within the surface of said cap, such that said calibrator housing is in flow communication with a flow of fluid.

13. A sensor calibrator in accordance with claim 5, wherein said calibrator housing further comprises an upper member that includes a first open end sized to receive at least a portion of the sensor therein.

14. A sensor calibrator in accordance with claim 13, wherein said upper member comprises at least one opening defined between an inner surface of said upper member and an outer surface of said upper member, said at least one opening sized to receive at least one fastener therein.

15. A calibrator assembly comprising:
   a sensor positioned within an inner surface of a calibrator assembly enclosure;
   a sensor calibrator positioned within said inner surface, said sensor calibrator coupled to said sensor; said sensor calibrator comprising:
      a calibrator housing comprising an outer surface and an opening defined therein, said calibrator housing removably coupled to said sensor, such that said opening provides flow communication between said sensor and ambient air; and
      a calibrator slide comprising a cavity defined therein, said calibrator slide positioned within said calibrator housing, said slide is slideably coupled to said calibrator housing and is movable between a first position and a second position, said slide contacts said sensor in the second position, such that a chamber is defined between said slide and said sensor; and
   a calibrator canister coupled to an outer surface of the calibrator assembly enclosure by a gas line and an outlet port, said sensor calibrator coupled in flow communication with said calibrator canister.

16. A calibrator assembly in accordance with claim 15, wherein said calibration canister comprises at least one of a calibration gas and/or a clean gas.

17. A calibrator assembly in accordance with claim 15, wherein said calibration slide is positioned a distance from said sensor in a first position, such that said sensor is in flow communication with interior area ambient air through said housing opening.

18. A calibrator assembly in accordance with claim 15, wherein said sensor calibrator further comprises: a diffuser coupled to said calibrator slide, said diffuser positioned within said calibrator slide cavity and configured to channel a fluid to said sensor, such that the fluid has a substantially uniform velocity.

19. A calibrator assembly in accordance with claim 15, wherein said calibrator slide comprises a base member comprising an orifice defined therein, said orifice configured to channel a fluid to said sensor at a predetermined flowrate.

* * * * *